United States Patent [19]

Kawasaki et al.

[11] Patent Number: 5,425,716
[45] Date of Patent: Jun. 20, 1995

[54] INFUSION APPARATUS

[75] Inventors: Tatsuro Kawasaki, Miyazaki; Yoshishige Yamashita, Kuki; Kazuo Matsubara, Tokyo, all of Japan

[73] Assignee: Atom Kabushiki Kaisha, Tokyo, Japan

[21] Appl. No.: 39,031
[22] PCT Filed: Aug. 10, 1992
[86] PCT No.: PCT/JP92/01025
 § 371 Date: May 20, 1993
 § 102(e) Date: May 20, 1993

[30] Foreign Application Priority Data

Aug. 9, 1991 [JP] Japan .................................. 3-224743
Aug. 9, 1991 [JP] Japan .................................. 3-224744
Aug. 9, 1991 [JP] Japan .................................. 3-224750

[51] Int. Cl.$^6$ ............................................. A61M 1/00
[52] U.S. Cl. .................... 604/152; 604/121; 604/67; 128/DIG. 12
[58] Field of Search ............... 128/DIG. 1, DIG. 12, 128/DIG. 13; 604/65, 66, 67, 151, 154

[56] References Cited

U.S. PATENT DOCUMENTS

| | | | |
|---|---|---|---|
| 3,701,345 | 10/1972 | Heilman et al. | 604/66 |
| 4,529,401 | 7/1985 | Leslie et al. | 604/67 |
| 4,617,637 | 10/1986 | Chu et al. | 128/205.18 |
| 4,652,260 | 3/1987 | Fenton, Jr. et al. | 604/154 |
| 4,767,406 | 8/1988 | Wadhom et al. | 604/67 |
| 4,976,696 | 12/1990 | Sanderson et al. | 604/65 |
| 4,978,335 | 12/1990 | Arthur, III | 604/67 |
| 4,988,337 | 1/1991 | Ito | 604/154 |
| 5,034,004 | 7/1991 | Crankshaw | 604/67 |
| 5,242,408 | 9/1993 | Jhuboo et al. | 604/67 |
| 5,295,967 | 3/1994 | Rondelet et al. | 604/67 |

Primary Examiner—C. Fred Rosenbaum
Assistant Examiner—Perry E. Van Over
Attorney, Agent, or Firm—Parmelee, Bollinger & Bramblett

[57] ABSTRACT

Infusion apparatus is provided for discriminating the specifications of syringes of any manufacturer, setting alarm levels corresponding to contained liquid solutions having various viscosities, and obtaining a net pressure for infusion from the force to a plunger by considering pressure loss dependent on a friction factor between the barrel and the plunger of the syringe. Syringe diameter is detected digitally to determine a capacity signal. The plunger force is detected by a pressure sensor and then A/D converted to a digital pressure signal. Specifications of syringes of manufacturers based on the syringe capacity signal are compared with the signals of the mounted syringe to select one among operation programs corresponding to their syringe specifications. A Dip switch selects a group of the operation programs for manufacturers. The digital pressure signal from the pressure converter is input to a comparator through a subtracter cooperating with a pressure loss constant table to compare outputs from a supremum constant table indicating the needle for the infusion solution is correctly injected into the blood vessel or muscle of the patient. A pressure loss is subtracted from the force detected based on the friction factor and the output from the pressure converter produces a value corresponding to the net pressure.

9 Claims, 6 Drawing Sheets

INFUSION APPARATUS

TECHNICAL FIELD

The present invention relates to an infusion apparatus for injecting various types of medicinal solutions or blood into a human body by using a syringe type injection pump.

BACKGROUND ART

Infusion apparatuses, e.g., pumps, for automatically performing infusion by using syringes are conventionally known. A medicinal solution in a medicine bottle is drawn into the syringe through a needle. Alternatively, a medicine cartridge is stored in the syringe. After the syringe containing the medicinal solution is mounted on the pump, a syringe plunger is pushed by a slider of the pump at a constant rate, so that the infusion solution is automatically administered to the patient. Infusion apparatuses of this type are disclosed in JP-A-48-62289, JP-U-57-76637, and JP-B-63-443390.

In such an infusion apparatus, a medicinal solution or blood must be reliably injected at a predetermined flow rate to the patient without an abnormality. Thus, in the conventional infusion apparatus, a slider for pushing the plunger is controlled by using, e.g., a microcomputer system. In another conventional infusion apparatus, the supremum pressure at the needle is determined immediately before the medicinal solution is injected to the patient. The force to the plunger is then expected and calculated at the supremum. An alarm is produced or the operation of the pump is stopped when this supremum force is detected.

syringes used in the infusion apparatus are manufactured by various manufacturers. Their sizes or configurations are standardized to a certain degree. However, the syringes of different manufacturers have different inherent slidable or dynamic frictional resistance values. Accordingly, it needs various specification data, e.g., the slidable frictional resistance, stroke, and capacity of the syringes. The various specification data therefore can be stored by using an EPROM or the like. When data on the slidable frictional resistance of the syringe of a certain manufacturer is stored in the EPROM of one infusion apparatus, its apparatus adapts to that of the syringes according to the specifications of the manufacturer.

In the conventional infusion apparatus, however, even when the force to the plunger exceeds the supremum force to produce the alarm, sometimes no abnormality occurs. This is because injecting pressure changes are not considered, which depend on the viscosity of the medicinal solution, the needle gauge or size, and the injecting location (vein, artery or muscle) of the patient. More specifically, since the supremum force is set according to a medicinal solution having a low viscosity, it does not correspond to a high-calorie medicinal solution having a high viscosity that attracts attention lately. Also, the supremum force does not correspond to a reaction against the injecting pressure when a needle having a small gauge and thus a large pressure loss is used, and when injection into an artery is performed, which are influenced by the blood pressure. In a worst case, when the patient takes a sudden turn for the worse and the blood pressure is increased, infusion is sometimes stopped by an alarm.

Also, in the conventional infusion apparatus, an alarm is sometimes produced before the force to the plunger reaches a predetermined supremum, and the operating pump is stopped. This is because the friction factor between the barrel and the plunger is not considered. More specifically, to determine the net injection amount of the infusion solution from the force to the plunger, it is indispensable to consider the friction factor between the barrel and the plunger slidably mounted thereto.

Furthermore, since the conventional infusion apparatus employs a small capacity EPROM, it cannot store all the specification data of the syringes of different manufacturers and all the operation programs for use in these syringes. Therefore, different standard EPROMs for different manufacturers must be used. Hence, a label must be adhered to the infusion apparatus to indicate that this apparatus corresponds to the syringe of a specific manufacturer, thereby clarifying the syringe of which manufacturer can be used in this infusion apparatus. If a syringe of a manufacturer to which the infusion apparatus does not correspond is erroneously used, problems occur because the specification data of the syringe is different. Then, a medicinal solution cannot be supplied at a preset flow rate. Various types of alarm units provided for safety infusion operation are malfunctioned.

The present invention, made in view of the above situations, has as its object to provide an infusion apparatus for obtaining a net pressure for infusion from the force to a plunger by considering the friction factor between the syringe barrel and the plunger.

It is another object of the present invention to provide an infusion apparatus capable of switching the alarm level of the injection pressure over a plurality of levels by considering reactions caused by the viscosity of the medicinal solution, the gauge of the needle, and the injecting location (vein, artery or muscle) of the patient.

It is still another object of the present invention to provide a highly reliable, simple infusion apparatus which can reliably correspond to syringes, and inject a medicinal solution at a preset flow rate to the patient even when these syringes having various specifications are used.

An infusion apparatus according to the present invention comprises a syringe for storing a medicinal solution, driving means for pushing a plunger in the syringe barrel at a predetermined speed, a pressure sensor for detecting a force to the plunger, a comparator capable of receiving an output from the pressure sensor, supremum and lowest limit constant tables each connected to inputs of the comparator, and a selection switch for selecting supremum and lowest limit values output from the supremum and lowest limit constant tables. A signal from the pressure sensor or an analog signal is A/D converted into, e.g., an 8-bit digital signal by a pressure converter.

According to another embodiment, an apparatus may further comprise a learning function of updating the supremum and lowest limit values corresponding to an alarm produced within a predetermined period after infusion is started.

An infusion apparatus according to another embodiment comprises a syringe for storing a medicinal solution, driving means for pushing a plunger into the syringe barrel at a predetermined speed, a pressure sensor for detecting a force to the plunger, a pressure converter connected to a signal output from the pressure sensor, a pressure loss constant table for outputting a pressure loss based on a friction factor between the barrel and the plunger, and a subtracter for subtracting the pressure loss from a detected force output from the pressure converter to obtain a net pressure.

According to still another embodiment, an apparatus may further comprise a learning function of storing, as the pressure loss, a force obtained when the plunger in the empty syringe is pushed at the predetermined speed, in the pressure loss constant table in a RAM. The friction factor is determined based on the standards and manufacturer specifications of the syringe. Accordingly, various values are stored in the ROM.

An infusion apparatus according to this still another embodiment of the present invention, in which a movable slider is abutted on a syringe plunger, and the plunger is pushed by moving the slider, comprises driving means for pushing the slider at a predetermined speed, means for detecting a force to the plunger, syringe diameter means for detecting a capacity of the syringe, data storage means for storing specification data for various syringes, program storage means for storing operation programs for said various syringes, comparing means for comparing information output from the pressure sensor and the syringe diameter means, with the specification data of the syringes stored in the storage means to determine a specific syringe to be mounted, and switching means for selecting a predetermined operation program for said specific syringe among the operation programs stored in the program storage means according to a comparison result of the comparing means.

BEST MODE OF CARRYING OUT THE INVENTION

Preferred embodiments of an infusion apparatus according to the present invention will be described with reference to the accompanying drawings.

Figure 1:
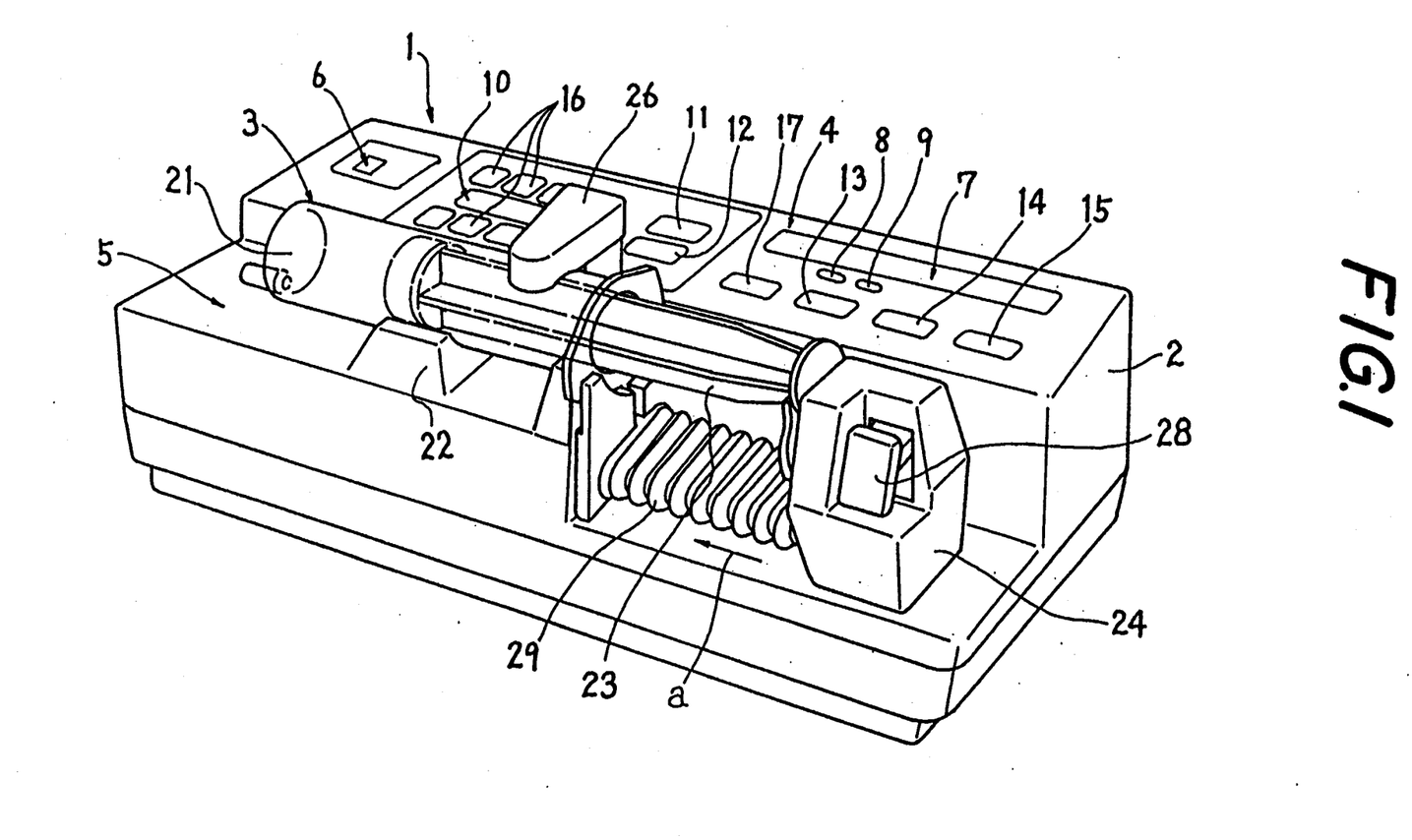
FIG. 1 is a perspective view showing the outer appearance of an infusion apparatus according to an embodiment of the present invention.

FIG. 1 shows the outer appearance of an infusion apparatus 1 according to an embodiment of the present invention. Provided on a case 2 of the infusion apparatus 1 are an operating section 4 for monitoring the infusion operation of a syringe 3 and the infusion state of the syringe 3, and a mount section 5 on which the syringe 3 can be mounted. As the syringe 3, a standard product having a total capacity of, e.g., 10 mm, 20 mm, 30 mm, or 50 mm is used according to the application. Thus, the syringe 3 has an outer diameter corresponding to the standard. Standard 50-ml syringes 3 of different manufacturers have different coefficients of friction with respect to the plunger, and have different pressures per unit flow rate. However, syringes of the same standard manufactured by the same manufacturer have substantially no variation in friction factor, and thus have a substantially constant friction factor.

A capacity indicator 6, a centralized indicator 7, an infusion start indicator 8, an infusion stop indicator 9, and a four-digit numerical indicator 10 are disposed on the operating section 4. The capacity indicator 6 indicates the size of the mounted syringe 3 by, e.g., an LED. The centralized indicator 7 indicates various operating states. The numerical indicator 10 indicates the flow rate, accumulated flow rate, or one-shot flow rate during infusion by a unit of ml/hr (time) or ml.

Thus, the centralized indicator 7 has a test or self-diagnostic indicator, an automatic alarm level set indicator, and a clogging/open indicator. The self-diagnostic indicator indicates a self-diagnostic program run. The automatic alarm level set indicator is turned on for a predetermined period, after infusion is started, to indicate that the supremum and lowest limit alarm values are updated. The clogging/open indicator is turned on when an abnormality occurs during infusion, e.g., when the needle is clogged or accidentally removed after the predetermined period elapses. The centralized indicator 7 also has a low-voltage indicator, an erroneous operation indicator, an infusion completion indicator, and a stand-by indicator. The low-voltage indicator indicates that an incorporated secondary cell reaches its use limit. The erroneous operation indicator indicates an erroneous operation sequence. The infusion completion indicator indicates completion of infusion. The stand-by indicator indicates that completion of infusion is within one minute.

In addition, a one-shot button 11, an infusion amount button 12, an infusion start/stop button 13, a fast-feed button 14, and a power supply button 15 are disposed on the operating section 4. The one-shot button 1 can feed a larger amount of infusion solution than an ordinary infusion amount when an emergency occurs. The infusion amount button 12 is used to select the indicated content of the numerical indicator 10. Furthermore, flow rate set buttons 16 for setting the flow rate in units of digits are disposed above and under the numerical indicator 10. The flow rate set buttons 16 can be set to 0.0 to 199.9 ml/hour. A learning function set button 17 or buzzer stop button (not shown) is also disposed on the operating section 4. When the plunger in the empty syringe 3 is pushed at a constant speed, the pressure of this time is regarded as the pressure loss and stored in a pressure loss constant table by the operation of the learning function set button 17 or buzzer stop button.

Figure 2:
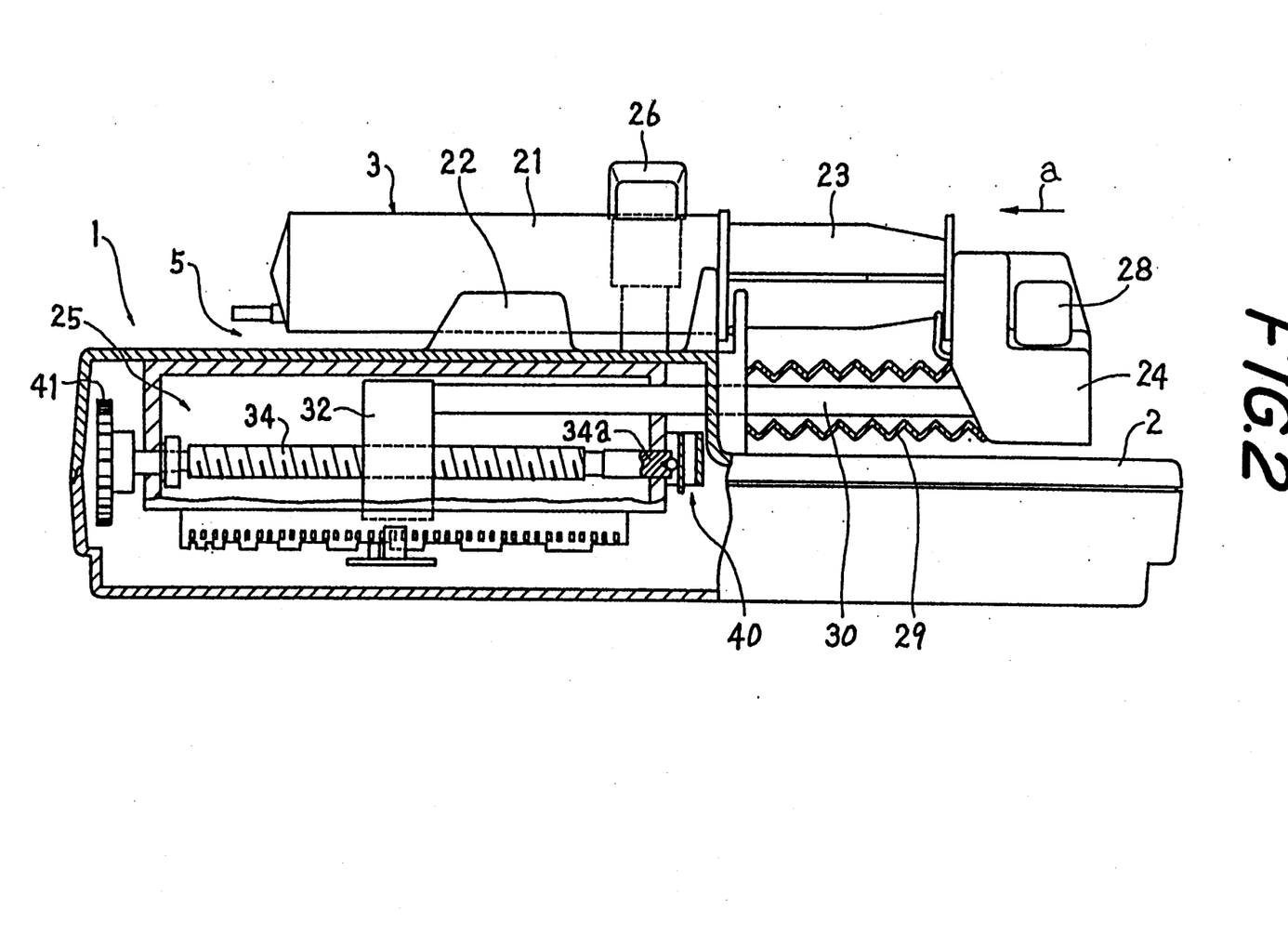
FIG. 2 is a partially cutaway sectional view of the infusion apparatus shown in FIG. 1.

Referring to FIG. 2, the mount section 5 includes a rest portion 22 on which a barrel 21 of the syringe 3 is placed. A plunger 23 slidably movable in the barrel 21 can be pushed by a slider 24. A driving means 25 transports the slider 24 toward the rest portion 22 (in a direction of an arrow a) while supporting it. A holder 26 for fixing the placed syringe 3 from above is formed on the rest portion 22. A syringe diameter detector 27 is disposed under the holder 26. A release button 28 for releasing the driving means 25 and restoring the slider 24 to the initial position is provided to the slider 24. Part of the driving means 25 is covered with a bellows 29 so that the interior of the driving means 25 cannot be seen.

Accordingly, in the pump having the syringe 3, the barrel 21 is held by the holder 26 and the rear end portion of the plunger 23 is abutted to the slider 24. A flexible infusion pipe (not shown) communicating with the needle is connected to the distal end of the syringe 3. Hence, when the syringe 3 is mounted on the rest portion 22 and the slider 24 is caused by the driving means 25 to push the plunger 23 at a predetermined speed in the direction of the arrow a, the medicinal solution in the syringe 3 is pushed out at a predetermined flow rate, and injected to the patient through the infusion pipe and the needle.

FIG. 2 also shows the driving means 25 of the slider 24 and a pressure sensor 40 for detecting a pressure obtained when the medicinal solution is injected to the patient. The driving means 25 has a main shaft 30 slidably supported in the mount section 5, and a release shaft slidably supported in the mount section 5 and parallel to the main shaft 30. One end of the main shaft 30 is fixed to the slider 24, and the other end thereof is fixed to an engaging member 32. The release shaft is not seen because of disposing behind the main shaft 30. The release shaft has one end portion axially supported by the slider 24, the other end portion axially supported by the engaging member 32, one end fixed to the release button 28 through an arm, and the other end fixed to the engaging pawl (not shown) of the engaging member.

The engaging member 32 is slidably supported in the mount section 5 and reciprocally moved by a feed screw 34, engageable with the engaging pawl, in the same manner as the slider 24. More specifically, the engaging member 32 is slidably mounted on a guide rod and the feed screw 34 that are disposed parallel to the main shaft 30 and the release shaft in the mount section 5. The feed screw 34 is axially supported in the mount section 5 to be slightly movable in the axial direction. The guide rod (not shown) is disposed in front of the feed screw 34. Since the engaging member 32 and the slider 24 are slidably supported in the mount section 5 by the release rod and the feed screw 34, the guide rod can be eliminated.

Figure 3:
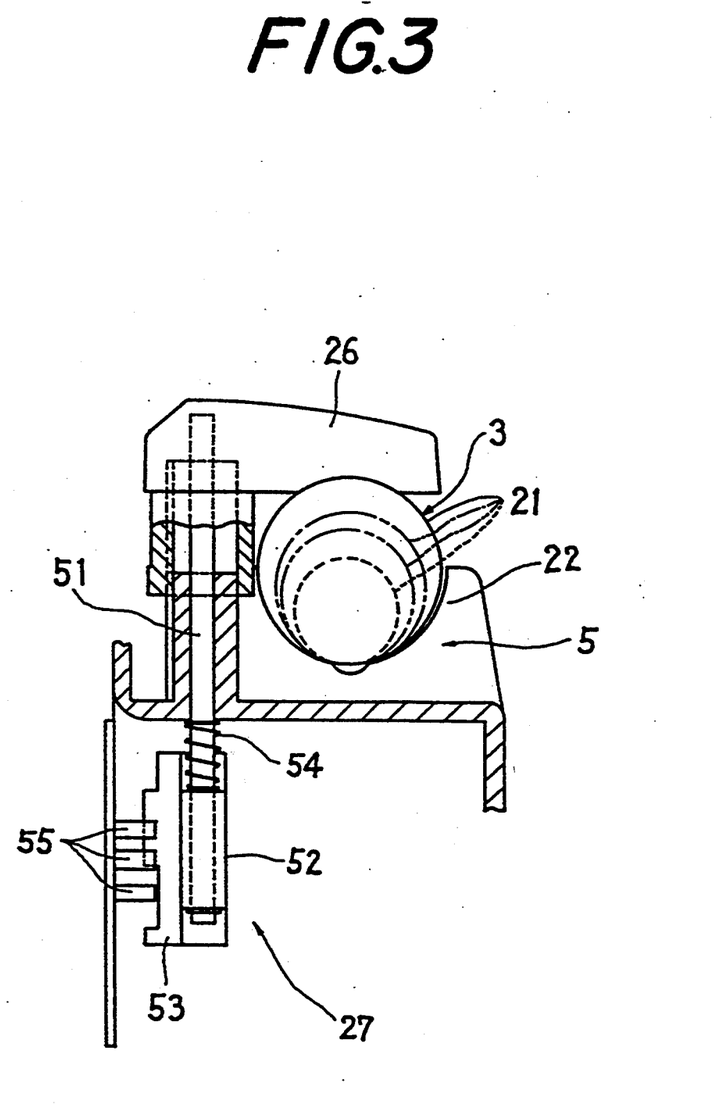
FIG. 3 is a sectional view showing a syringe diameter means for detecting the capacity of a syringe.

FIG. 3 shows the syringe diameter means 27 for detecting the capacity of the syringe 3. Syringes 3 used in this infusion apparatus are manufactured by various manufacturers, but the diameter of the syringe 3 corresponding to the capacity of the syringe 3 is determined by standards. Accordingly, syringes 3 having the same capacity have the same diameter even if they are manufactured by different manufacturers.

The syringe diameter means 27 includes a coupling shaft 51, a mount member 52, a blocking plate 53, and a plurality of opto-couplers 55. The coupling shaft 51 is vertically moved in the interlocked manner to the holder 26 that holds the barrel 21 of the syringe 3. The mount member 52 is provided under the coupling shaft 51 and serves to mount the blocking plate. The blocking plate 53 has notches. Each opto-coupler 55 comprises an LED, a photodetector and a groove corresponding to the blocking plate 53. The holder 26 is biased downward by a spring 54.

In this case, three or upper, middle and lower photointerrupters or opto-coupler 55 are used to detect four syringes 3 each having different capacity. FIG. 3 shows barrels 21 of a 50-ml syringe 3, a 30-ml syringe, a 20-ml syringe, and a 10-ml syringe with solid, dot-dash, dot-dot-dash and broken lines, respectively. A plurality of notches are formed in the blocking plate 53. The widths of the notches are determined such that the photodetector of the lower opto-coupler 55 is exposed upon mounting the 50-ml syringe 3; all the three photodetectors thereof are shielded by the plate 53 upon mounting the 30-ml syringe 3; the upper photodetector is exposed upon mounting the 20-ml syringe 3; and the upper and middle photodetectors among the three opto-couplers 55 are exposed upon mounting the 10-ml syringe 3. When a syringe 3 is not mounted, all the photodetectors of the three opto-couplers 55 are exposed. In this manner, information representing the capacity and presence/absence of the syringe 3 is output from the syringe diameter means 27.

Alternatively, the widths of the notches of the blocking plate 53 may be set such that all the photodetectors are shielded when any syringe is not mounted; only the lower photodetector (001) is exposed when the 10-ml syringe 3 is mounted; the middle and lower photodetectors (011) are shielded when the 20-ml syringe 3 is mounted; all the photodetectors (111) are exposed when the 30-ml syringe 3 is mounted; and only the lower photodetector (110) is shielded when the 50-ml syringe 3 is mounted. Accordingly, the syringe diameter detector 27 has a decoder for receiving a 3-bit wide digital signal from the three photodetectors, and decoding its digital signal into a 1-bit signal representing presence/absence of the syringe and a 2-bit diameter signal R representing the type of the syringe and outputting them.

Figure 4:
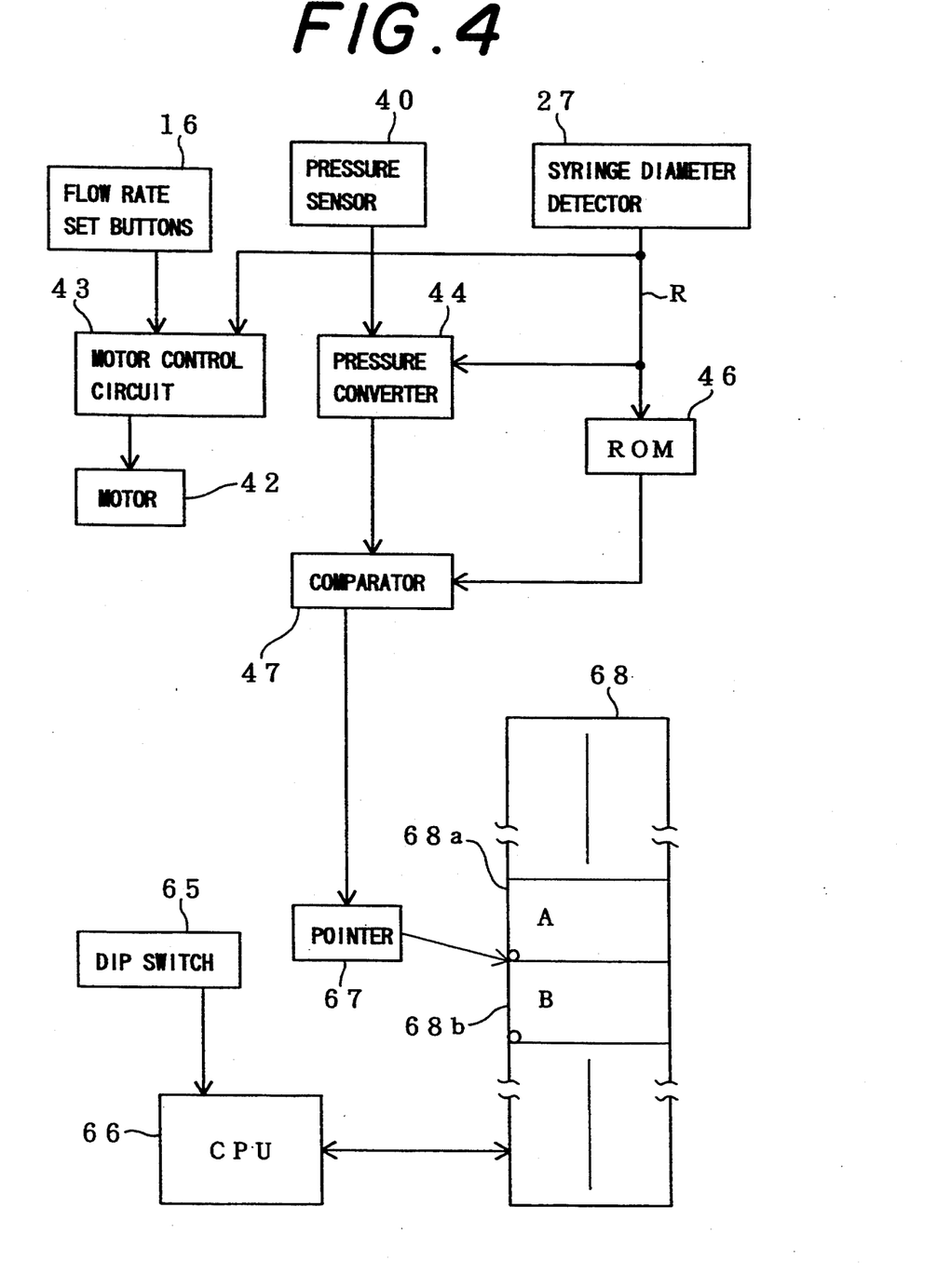
FIG. 4 is a block diagram schematically showing the infusion apparatus according to the first embodiment of the present invention.

Referring again to FIG. 2, the feed screw 34 has one end 34a mounted on a pressure sensor 40 through a hard ball, and the other end fixed to a gear wheel 41 of a reduction gear mechanism. The gear wheel 41 meshes with a pinion. As shown in FIG. 4, under the control of a motor control circuit 43, a motor 42 having a rotating shaft fixed to the pinion is rotated at a preset speed by a flow rate signal sent from the flow rate set buttons 16 and the diameter signal R. The flow rate signal and the diameter signal R are stored in a memory or RAM.

The slider 24 is moved by the feed screw 34, driven based on the preset flow rate, to push the plunger 23 of the syringe 3 in the direction of the arrow a, thereby pushing out a medicinal solution at a predetermined flow rate. The reaction of the pushing force of the slider 24 on the plunger 23 is transmitted to the feed screw 34 through the coupling member 30 and the driven member 32, and the pressure sensor 40 electrically converts this reaction into a pressure signal and outputs it.

FIG. 4 is a block diagram of the infusion apparatus according to the first embodiment of the present invention. The infusion apparatus 1 determines the infusion state based on the pressure signal output from its pressure sensor 40, and performs control to stop infusion. The pressure signal output from the pressure sensor 40 is amplified by an amplifier and input to a pressure converter 44.

A ROM (data storage means) 46 stores specification data of syringes manufactured by various manufacturers. A program storage means 68 stores operation programs corresponding to the syringes manufactured by the various manufacturers. For example, an operation program corresponding to a syringe available from a manufacturer A is stored in a program area 68a. Another operation program corresponding to a syringe available from a manufacturer B is stored in a program area 68b.

A Dip switch 65 serves to perform an initial setup operation of the syringe employed in the infusion apparatus. According to the setup operation by the Dip switch 65, a CPU 66 selects an operation program stored in the program storage means 68. For example, when a setup operation is performed by the Dip switch 65 to use the syringe available from the manufacturer A, the CPU 66 selects the program area 68a storing the operation program corresponding to the syringe of the manufacturer A.

In response to the setup operation by the Dip switch 65, the ROM 46 outputs predetermined specification data from stored specification data of the syringes manufactured by the various manufacturers.

When a syringe is placed and the infusion apparatus is operated, the syringe diameter means 27 detects the capacity of the syringe, and the motor control circuit 43 outputs a control signal to the motor 42 so that infusion is performed at a preset flow rate. Upon start of infusion, the pressure sensor 40 detects the force to the plunger or inner-pressure of the infusion solution and outputs a detected pressure signal to the pressure converter 44. The pressure converter 44 outputs various types of information signals to a comparator 47 based on the signals obtained from the pressure sensor 40 and the syringe diameter means 27. The ROM 46 outputs the specification data of the syringe to the comparator 47, and the comparator 47 compares information output from the pressure converter 44 with information output from the ROM 46.

When a predetermined syringe is mounted on the infusion apparatus and a test or self-diagnostic operation is performed, the slider starts moving to push the plunger. Information on the slidable frictional resistance and the like of the syringe obtained at this time and data stored in the ROM (data storage means) 46 are compared by the comparator 47. If the comparison result is correct, the operation of the infusion apparatus can be continued. When a syringe having specifications different from those of the initially set syringe is mounted on the infusion apparatus and a test operation is performed, the slider starts moving to push the plunger, in the same manner as the test operation described above. Information on the slidable frictional resistance and the like of the syringe obtained at this time and data stored in the ROM 46 are compared by the comparator 47. If the comparison result is determined to be incorrect, the operation of the infusion apparatus is automatically interrupted.

If an alarm sound is produced at this time, the operator of the infusion apparatus notices the erroneous operation. Alternatively, a coded error message may be indicated by using the numerical indicator 10 shown in FIG. 1. For example, when a syringe of the manufacturer B is mounted on an infusion apparatus preset to correspond to a syringe of the manufacturer A, the infusion apparatus produces an alarm sound to inform the operator of this fact. The operator recognizes the erroneous operation and performs a correct operation. For example, if a syringe of the manufacturer A is available at hand, he may mount it on the infusion apparatus. If only the syringe of the manufacturer B is available at hand, he may operate the Dip switch 65 to change the initial setting of the infusion apparatus to select the program area 68b storing the operation program corresponding to the syringe of the manufacturer B and stored in the program storage means 68.

According to the infusion apparatus of the present invention, the specification data of syringe having various specifications manufactured by various manufacturers are stored in the ROM 46. Hence, by switching the Dip switch 6 5 to designate change of the initial setup, operation programs stored in the program storage means 68 and corresponding to syringes having various specifications are selected, and predetermined specification data of the specification data of the syringes having various specifications stored in the ROM 46 are selected.

When the test operation is performed, the specifications of the mounted syringe and the specification data of the syringes having various specifications stored in the ROM 46 may be compared to discriminate the specifications of the mounted syringe. Then, an operation program capable of corresponding to a specific one of the syringes having various specifications stored in the program storage means 68 may be automatically selected by a pointer 67.

The infusion apparatus according to the first embodiment of the present invention has a ROM (data storage means) for storing the specification data of the syringe have various specifications that can be mounted. Hence, the ROM need not be exchanged for causing the infusion apparatus to correspond to syringes having various specifications. Since the initial setup can be changed by the Dip switch, even when a syringe different from an initially set syringe is mounted, it can be coped with by only switching the Dip switch. Furthermore, the specification data stored in the ROM and the data of the mounted syringe are compared by the comparator to determine the specifications of this syringe. Then, a predetermined operation program of the operation programs stored in the program storage means can be automatically selected by the pointer.

Figure 5:
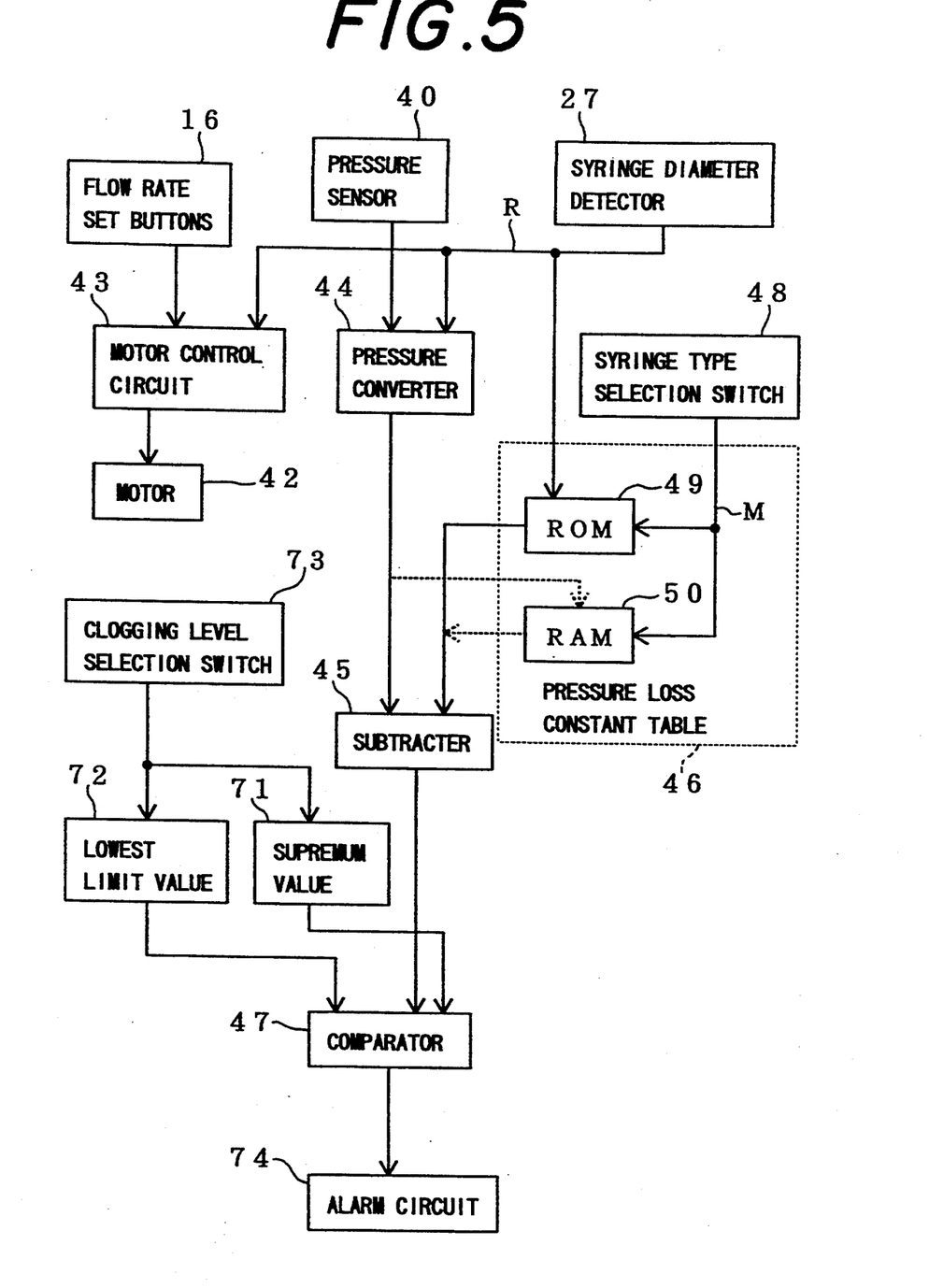
FIG. 5 is a block diagram schematically showing an infusion apparatus according to the second embodiment of the present invention.

FIG. 5 shows an infusion apparatus according to the second embodiment of the present invention. Referring to FIG. 5, members corresponding to those shown in FIG. 4 are denoted by the same reference numerals, and a detailed description of the corresponding members will be omitted.

A pressure signal output from a pressure sensor 40 is amplified by an amplifier and input to a pressure converter 44. After A/D conversion, the pressure converter 44 converts the pressure difference caused by a difference in syringe diameter based on a 2-bit diameter signal R, thereby obtaining a pressure per unit area of the medicinal solution. An output from the pressure converter 44 is input to a subtracter 45.

The subtracter 45 also receives an output from a pressure loss constant table 46 which outputs a pressure loss based on a friction factor between a barrel 22 and a plunger 23. The pressure loss constant table 46 has a ROM 49 for receiving, e.g., a 3-bit manufacturer signal M output from a syringe type selection switch 48. For example, the 2-bit diameter signal R corresponding to four different syringe diameters is input to the ROM 49. Then, a pressure loss corresponding to a syringe having a specific diameter, currently in use, of a specific manufacturer is input to the subtracter 45. Accordingly, a value concerning the friction factor to be stored in the ROM 49 is determined based on the standards and manufacturer specifications of the syringe 3.

In this another embodiment, a learning function is provided. According to this function, a pressure obtained when the plunger 23 in the empty syringe 3 is pushed at a constant speed is stored as a pressure loss in the pressure loss constant table 46. In this case, the pressure loss constant table 46 usually has a RAM or register 50 for storing the initial pressure value dependant on the friction factor obtained when the plunger 23 in the empty syringe 3 is pushed.

This learning function is effective in a case wherein the hospital usually uses the syringe 3 of a specific appointed manufacturer and a syringe 3 of another manufacturer must be used because of an emergency or of an inappropriate stock management. Accordingly, this learning function is practiced upon shipping from the factory if the hospital to which the syringes 3 are supplied is known in advance, or is practiced when the appointed manufacturer is changed by the hospital.

The output from the pressure loss constant table 46 is also input to the subtracter 45 and subtracted from the pressure value obtained upon injection, thereby obtaining a net pressure. This net pressure signal is output to a comparator 47 to prevent an adverse influence caused by the friction factor of the plunger 23 in the syringe 3. Alternatively, the pressure loss constant table 46 may have a learning function RAM or register 50 for storing a pressure value obtained when the plunger 23 in the empty syringe 3 is pushed at a constant speed.

The comparator 47 receives a clogging state detecting supremum value 71 indicating whether the needle for the infusion solution is correctly injected into the blood vessel or muscle of the patient, and an open state detecting lowest limit value 72 indicating whether the needle or an infusion pipe is removed by an external factor, e.g., when the patient turns over in the bed, and compares them with the net pressure signal. When these supremum and lowest limit values are digital values, they are supplied from the Dip switch or the ROM by the operation of a clogging pressure level selection switch 73, and changed according to the diameter signal R and the viscosity of the infusion solution.

When the pressure signal falls outside the range of the supremum and lowest limit values, the comparator 47 detects a corresponding abnormal state, and inputs an alarm signal to an alarm circuit 74. The alarm circuit 74 indicates an abnormal state on the clogging/open indicator 7 of FIG. 1 and supplies a stop signal ST to a motor control circuit 43 to stop a motor. Hence, the infusion state can always be monitored.

The alarm circuit 74 outputs alarm signals having various contents. For example, when a used syringe 3 is replaced with a fresh syringe 3 containing a new medicinal solution, the diameter of the used syringe 3 stored in advance and the diameter of the fresh syringe 3 are compared. If the comparison result is different, an alarm is produced. The alarm can be indicated in the form of sound, light, or the like depending on its contents. The respective circuits in FIG. 2 can be constituted by analog circuits, and a pulse motor can be used as the motor.

As described above, according the infusion apparatus of the second embodiment of the present invention, since a pressure loss constant table or a learning function considering the friction factor between the syringe barrel and the plunger is used, an accurate net pressure can be detected, a solution injection amount can be precisely detected, and an abnormality during infusion, e.g., removal of the needle or tube, and clogging of the needle, can be appropriately detected, so that safe infusion can always be performed.

Figure 6:
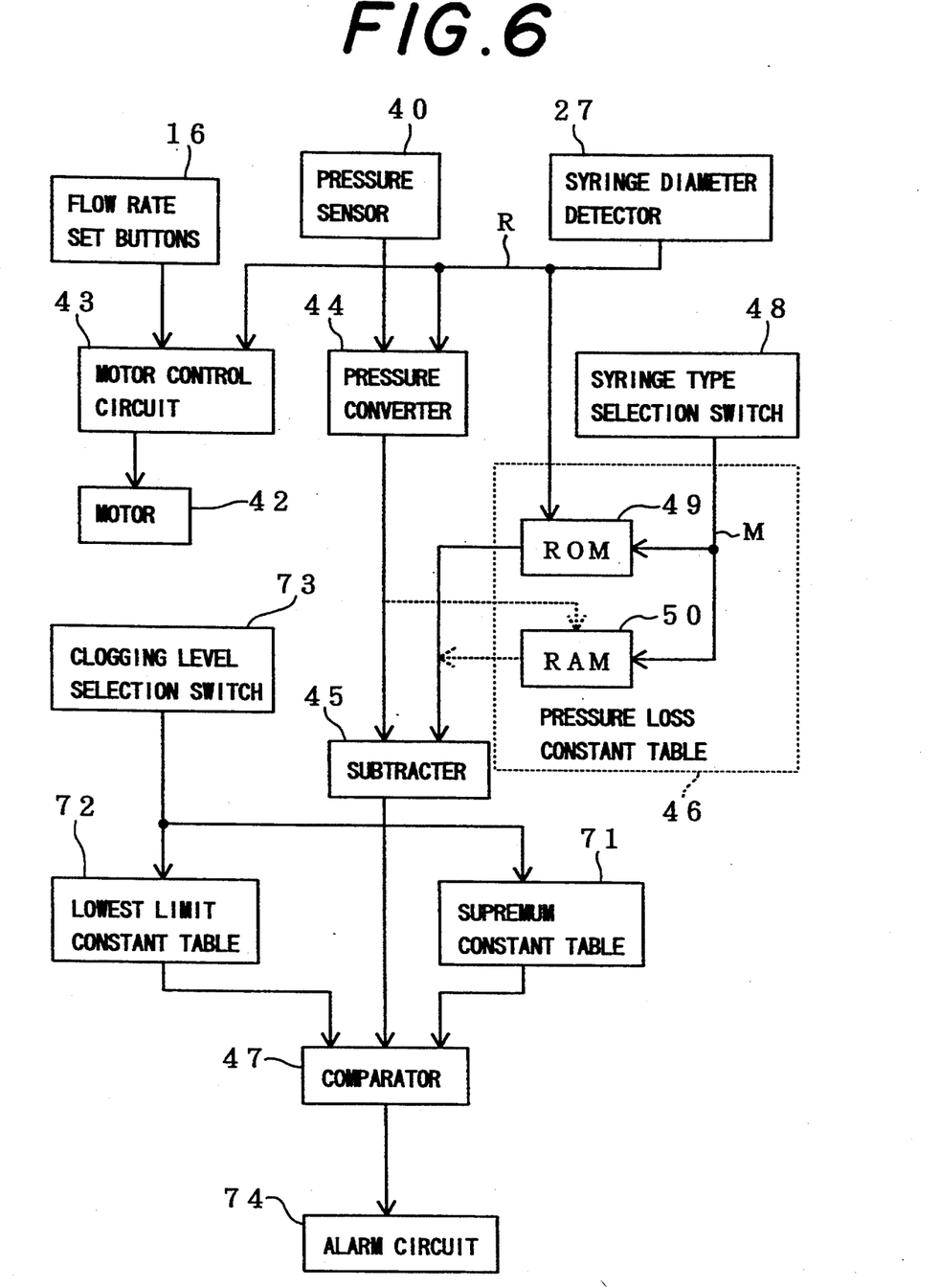
FIG. 6 is a block diagram schematically showing an infusion apparatus according to the third embodiment of the present invention.

FIG. 6 shows an infusion apparatus according to the third embodiment of the present invention. Referring to FIG. 6, members corresponding to those shown in FIG. 5 are denoted by the same reference numerals, and a detailed description of the corresponding members will be omitted.

A comparator 47 receives an output from a clogging state detecting supremum constant table 71 indicating whether the needle for the infusion solution is correctly injected into the blood vessel or muscle of the patient, and an output from an open state detecting lowest limit constant table 72 indicating whether the needle or an infusion pipe is removed by an external factor, e.g., when the patient turns over in the bed, and compares them with the net pressure signal.

The supremum and lowest limit constant tables 71 and 72 are ROMs or RAMs selected by a clogging pressure level selection switch 73 or a selection register. The clogging pressure level selection switch 73 outputs appropriate supremum and lowest limit values stored in the supremum and lowest limit constant tables according to the viscosity of the infusion solution, and is usually incorporated in the body so that it cannot be easily operated. The selection switch 73 can be manually operated by, e.g., a nurse to set, e.g., 16 alarm levels according to the gauge of the needle and the injecting location of the patient.

According to this another embodiment, when the needle is accurately inserted in the injecting location of the patient, the alarm level can be automatically set by using the fact that injection of the infusion solution reaches the stable state within a predetermined period, e.g., one minute after injection of the infusion solution is started. Within the predetermined period after infusion is started, when the output from the comparator 47 reaches the alarm level, the contents of the registers of the supremum and lower constant tables 71 and 72 are updated to select the alarm level of the next stage. Apparently, the learning function must monitor the condition of the patient under sufficient infusion after the predetermined period elapses. This function updates the supremum and lowest limits corresponding to an alarm that can be produced within the predetermined period after infusion is started.

The block circuit shown in FIG. 6 can use a one-chip microcomputer system or an ordinary microcomputer system having a CPU, a ROM, a RAM, an I/O unit, an A/D converting function, and a D/A converting function. However, the block circuit can be constituted by an analog circuit. In addition, a pulse motor can be used as the motor.

As described above, according the infusion apparatus of the third embodiment of the present invention, since the alarm level of the injection pressure is switched over a plurality of levels by considering the reaction caused by the viscosity of the medicinal solution, the gauge of the needle, and the injecting location (vein/artery/muscle) of the patient, alarm levels corresponding to infusion solutions having various viscosities can be set. Based on the alarm level, an abnormality during infusion, e.g., removal of the needle or tube, and clogging of the tube can reliably be detected, thereby constantly performing safe infusion.

What is claimed is:

1. An infusion apparatus comprising:
    a syringe for storing a medicinal liquid solution between a barrel and a movable plunger;
    means for mounting said barrel on said infusion apparatus;
    driving means for pushing said plunger in said barrel at a predetermined speed;
    a pressure sensor for detecting the force on said plunger to provide an analogue signal;
    a pressure converter for receiving and A/D converting said analogue signal to a digital pressure signal;
    a comparator having inputs capable of receiving said digital pressure signal from said pressure converter;

a supremum limit constant table having data outputs connected to other inputs of said comparator; and a selection switch for selecting a supremum limit value output from said supremum limit constant table.

2. An infusion apparatus according to claim 1, further comprising a learning function of updating the supremum value corresponding to an alarm produced within a predetermined period after infusion is started.

3. An infusion apparatus comprising:

a disposable syringe for storing a medicinal liquid solution between a barrel and a movable plunger;

means for mounting said barrel on said infusion apparatus;

driving means for pushing said plunger in said barrel at a predetermined speed;

a pressure sensor for detecting a force to said plunger to provide an analogue signal;

a pressure converter for receiving and A/D converting said analogue signal to a digital pressure signal;

a pressure loss constant table for outputting a pressure loss based on a friction factor between said barrel and said plunger; and a subtracter for subtracting the pressure loss from said digital pressure signal, thereby obtaining a net pressure to said plunger.

4. An infusion apparatus according to claim 3, further comprising a learning function of storing, as the pressure loss, a pressure obtained when said plunger in said empty syringe is pushed at the predetermined speed, in said pressure loss constant table.

5. An infusion apparatus according to claim 3, wherein the friction factor is determined based on standards and specifications of said syringe.

6. An infusion apparatus in which a movable slider is brought into contact with a plunger of a syringe having a barrel, said barrel mounted on a base, and said plunger is pushed by moving said slider relative to said base, comprising:

driving means for pushing said slider at a predetermined speed;

a pressure sensor for detecting a force to said plunger to provide an analogue signal;

a pressure converter for receiving and A/D converting said analogue signal to a digital pressure information;

syringe diameter means for detecting the capacity of said plunger to provide digital diameter information;

data storage means for storing specification data for various syringes;

program storage means for storing operation programs for said various syringes;

comparing means for comparing said information from said pressure sensor and said syringe diameter means, with the respective specification data of said syringes stored in said data storage means to determine a specific syringe to be mounted; and switching means for selecting a predetermined operation program for said specific syringe among said operation programs stored in the program storage means, according to a comparison result of said comparing means.

7. An infusion apparatus comprising:

a base;

a disposable syringe having barrel and plunger between which a medicinal solution is contained;

means for mounting said barrel on said base;

a movable slider abutted to said plunger to push said plunger;

a screw rod rotatably and axially-movably supported by said base and meshed with said movable slider;

a motor for rotating said screw rod; and a pressure sensor disposed between an end of said screw rod and said base to provide an analogue signal corresponding to a force to said plunger.

8. An infusion apparatus comprising:

a base;

a syringe having a movable plunger and a barrel detachably mounted on said base for storing a medicinal liquid solution;

driving means fixed to said base for pushing said plunger at a predetermined speed;

a pressure sensor associated with said drive means for detecting a force to said plunger to provide an analogue signal;

an analogue to digital converter receiving and A/D converting said analogue signal to an n-bits wide digital pressure signal, where n is a positive integer;

a comparator having n inputs capable of receiving said digital pressure signal;

a supremum limit constant table having n outputs connected to other n inputs of said comparator; and a selector for selecting an address of said supremum limit constant table to provide a predetermined supremum limit constant value.

9. An infusion apparatus in which a movable slider is brought into contact with a plunger of a syringe having a barrel, said barrel is mounted on a base, and said plunger is pushed by moving said slider relative to said base, comprising:

syringe diameter means for detecting a capacity of said plunger to provide digital diameter information;

data storage means for storing specification data of various types of syringes manufactured by various manufacturers;

switching means for selecting predetermined specification data for said various syringes of a predetermined manufacturer among said various manufacturers; and comparing means for comparing said information from said syringe diameter means, with said respective specification data of said syringes to determine which syringe has been mounted on said base.

* * * * *